US012588915B2

(12) United States Patent
Prieditis et al.

(10) Patent No.: US 12,588,915 B2
(45) Date of Patent: Mar. 31, 2026

(54) BONE RESECTION METHOD BY PLUNGE MILLING AND RASPING DURING TOTAL ANKLE ARTHROPLASTY

(71) Applicant: Arthrex, Inc., Naples, FL (US)

(72) Inventors: Maris Prieditis, Naples, FL (US); Benjamin Chan, Bonita Springs, FL (US); Adam N. Garlock, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 18/714,151

(22) PCT Filed: Dec. 2, 2022

(86) PCT No.: PCT/US2022/051613
§ 371 (c)(1),
(2) Date: May 29, 2024

(87) PCT Pub. No.: WO2023/102160
PCT Pub. Date: Jun. 8, 2023

(65) Prior Publication Data
US 2025/0032131 A1 Jan. 30, 2025

Related U.S. Application Data

(60) Provisional application No. 63/301,600, filed on Jan. 21, 2022, provisional application No. 63/285,722, filed on Dec. 3, 2021.

(51) Int. Cl.
*A61B 17/16* (2006.01)
*A61B 17/17* (2006.01)

(52) U.S. Cl.
CPC ...... *A61B 17/1659* (2013.01); *A61B 17/1682* (2013.01); *A61B 17/1775* (2016.11)

(58) Field of Classification Search
CPC ............ A61B 17/1659; A61B 17/1775; A61B 17/1682
See application file for complete search history.

(56) References Cited

U.S. PATENT DOCUMENTS 5,019,082 A    5/1991 Frey
D360,121 S  *  7/1995 Anderson ........................ D8/90
              (Continued)

FOREIGN PATENT DOCUMENTS

WO       2020239909 A2   12/2020

OTHER PUBLICATIONS

International Search Report and Written Opinion for corresponding PCT application No. PCT/US2022/051613 Apr. 14, 2013.

*Primary Examiner* — Sameh R Boles
(74) *Attorney, Agent, or Firm* — McDonnell Boehnen Hulbert & Berghoff LLP

(57) ABSTRACT

A system for tibial bone resection, comprising a device including a handle and a rasp coupled to the handle. The rasp includes a top surface, a bottom surface, a first side surface, and a second side surface. A portion of the top surface includes a first rough surface, a portion of the first side surface includes a second rough surface, and a portion of the second side surface includes a third rough surface. A first smooth curved surface separates the first rough surface from the second rough surface, and a second smooth curved surface separates the first rough surface from the third rough surface.

13 Claims, 9 Drawing Sheets

(56)     References Cited

U.S. PATENT DOCUMENTS

| 6,120,508 | A | * | 9/2000 | Grunig | ............... | A61B 17/1659 |
| | | | | | | 606/85 |
| D656,380 | S | | 3/2012 | Deleon | | |
| 2012/0029545 | A1 | * | 2/2012 | Nelson | ............... | A61B 17/1659 |
| | | | | | | 606/171 |
| 2013/0184713 | A1 | | 7/2013 | Bojarski | | |
| 2015/0157339 | A1 | | 6/2015 | McGinley | | |
| 2017/0348110 | A1 | | 12/2017 | May | | |
| 2021/0298911 | A1 | | 9/2021 | Dalton | | |
| 2021/0353313 | A1 | | 11/2021 | Lee | | |
| 2025/0032131 | A1 | * | 1/2025 | Prieditis | ............ | A61B 17/1659 |

* cited by examiner

157

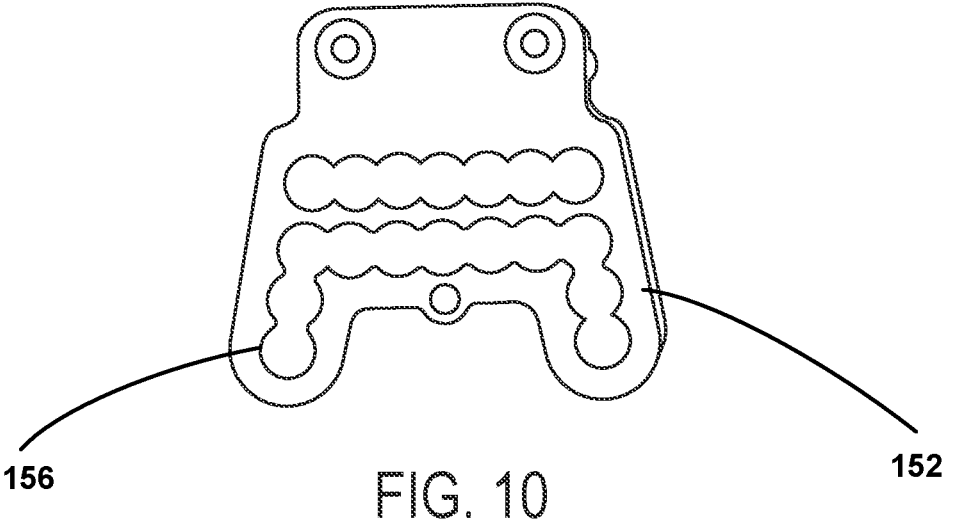
156                    FIG. 10                    152
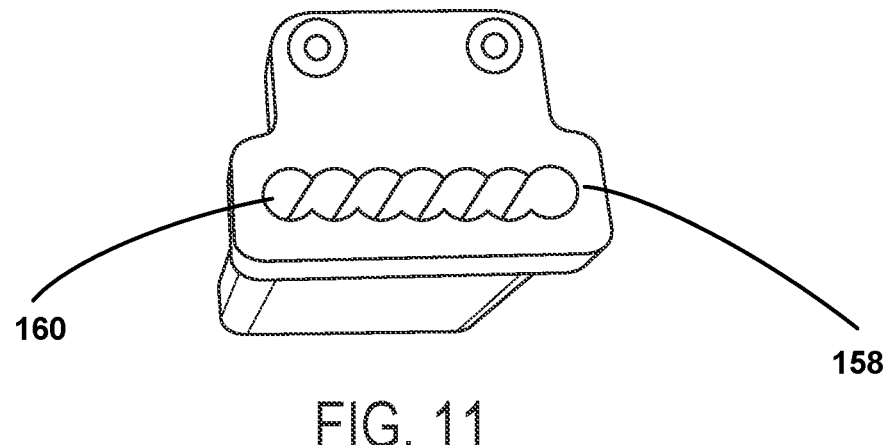
160
FIG. 11                    158

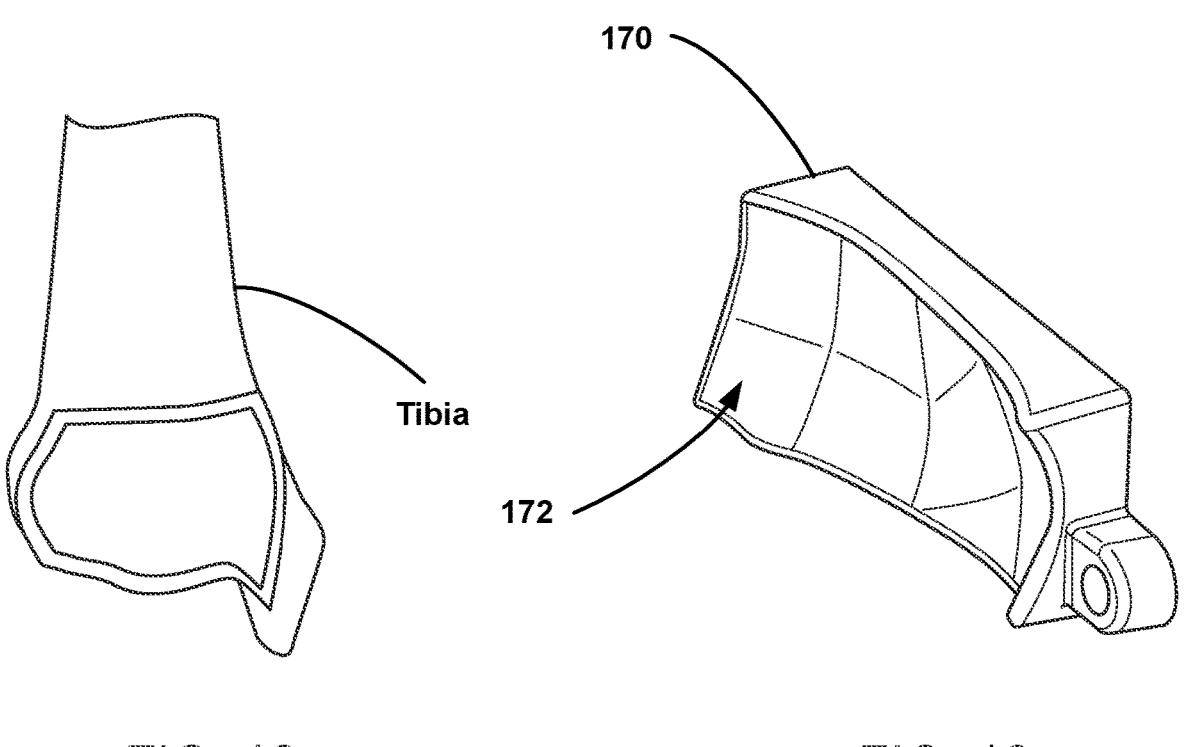
FIG. 12
FIG. 13
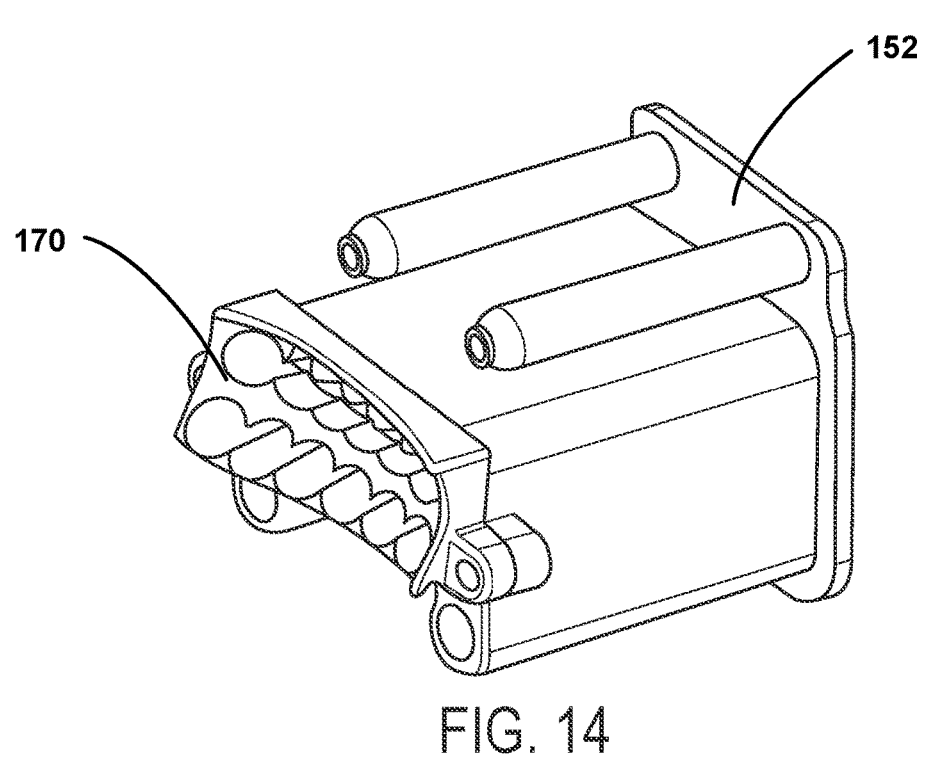
FIG. 14

Tibia

Tibia

100

BONE RESECTION METHOD BY PLUNGE MILLING AND RASPING DURING TOTAL ANKLE ARTHROPLASTY

CROSS-REFERENCE TO RELATED APPLICATIONS

This application claims the benefit of priority to (i) U.S. Provisional Application No. 63/285,722 entitled "Bone Resection Method by Plunge Milling and Rasping During Total Ankle Arthroplasty," filed on Dec. 3, 2021, and (ii) U.S. Provisional Application No. 63/301,600 entitled "Patient Specific Reamer Guides," filed on Jan. 21, 2022, the contents of each of which are hereby incorporated by reference in their entirety.

BACKGROUND

Total ankle replacement (TAR) requires precise tibial and talar bone resection that accommodates metal implants that will be fixed to prepared surfaces. Disclosed herein are instruments that aid in placing ankle implants.

SUMMARY

The present disclosure includes a system for tibial bone resection. Once a tibial bone has been resected, an implant may be fixed to a prepared surface of the tibia.

Further, the present disclosure includes a system for plunge milling a tibial bone, which may reduce vibration, generate less heat, is guided through bushings, and pulverizes resected bone as it is milled thereby obviating the problem of removing large bone fragments from the posterior tibiotalar joint capsule. A bone milling process reduces the degree of difficulty to resect a tibial bone required for TAR and potentially the time required for that removal when compared to traditional methods. Bone milling may also reduce the risk of adjacent tissue injury including thermal osteonecrosis, bone insult due to saw cut, nerve, and tendon laceration. An implant matched box rasp is designed to smooth out any remaining bone material left behind by the milling process. Medial and lateral corners of the implant matched rasps are polished smooth, making them incapable of gouging or digging into bone during rasping. These smooth medial and lateral corners match the placement of the two corner drill holes of the bushing and act as a guide for the rasp. These features mitigate the risk of over-rasping and removing more bone than is desired.

Thus, in a first aspect, a device includes a handle and a rasp coupled to the handle. A rasp includes a top surface, a bottom surface, a first side surface, and a second side surface. A portion of the top surface includes a first rough surface, a portion of the first side surface includes a second rough surface, and a portion of the second side surface includes a third rough surface. A first smooth curved surface separates the first rough surface from the second rough surface, and a second smooth curved surface separates first rough surface from the third rough surface.

In another aspect, the present disclosure provides a system including a first bushing configured to be removably coupled to a tibia of a patient. The first bushing includes a first plurality of through-holes. The system also includes a second bushing configured to be removably coupled to the tibia. The second bushing includes a second plurality of through-holes.

In another aspect, a method can include removably coupling a first bushing to a tibia of a patient, wherein the first bushing includes a first plurality of through-holes, plunging a reamer through the first plurality of through-holes and into the tibia, removably coupling a second bushing to the tibia of the patient, wherein the second bushing includes a second plurality of through-holes, plunging the reamer through the second plurality of through-holes and into the tibia, and removing additional tibia material using the device of any one of claims.

In another aspect, a system comprising a first bushing configured to be removably coupled to a tibia of a patient. The first bushing includes a first plurality of through-holes. The system also includes a patient specific disposable surface that is configured to be removably coupled to a first side of the first bushing. The system also includes a patient specific depth guide that is configured to be removably coupled to a second side of the first bushing. The patient specific depth guide includes a plurality of through-holes that align with the first plurality of through-holes of the first bushing.

In another aspect, a method can include removably coupling a first bushing to a tibia of a patient, wherein the first bushing includes a first plurality of through-holes, removably coupling a patient specific disposable surface to a first side of the first bushing, removably coupling a patient specific depth guide to a second side of the first bushing, wherein the patient specific depth guide includes a plurality of through-holes that align with the first plurality of through-holes of the first bushing, and plunging a reamer through the first plurality of through-holes, through the patient specific disposable surface, and into the tibia of the patient.

In yet another aspect, a kit includes the devices and the systems disclosed herein.

BRIEF DESCRIPTION OF THE DRAWINGS

FIG. 10 is a perspective view of an example first bushing

FIG. 11 is a perspective view of an example second bushing for use in combination with the first bushing of FIG. 10.

FIG. 12 is a scan of a distal tibia of a patient.

FIG. 13 is a patient specific disposable surface created based on the scan of the distal tibia of the patient of FIG. 12.

FIG. 14 is a perspective view of the patient specific disposable surface removably coupled to a first side of a bushing after reaming.

DETAILED DESCRIPTION

Figure 1:
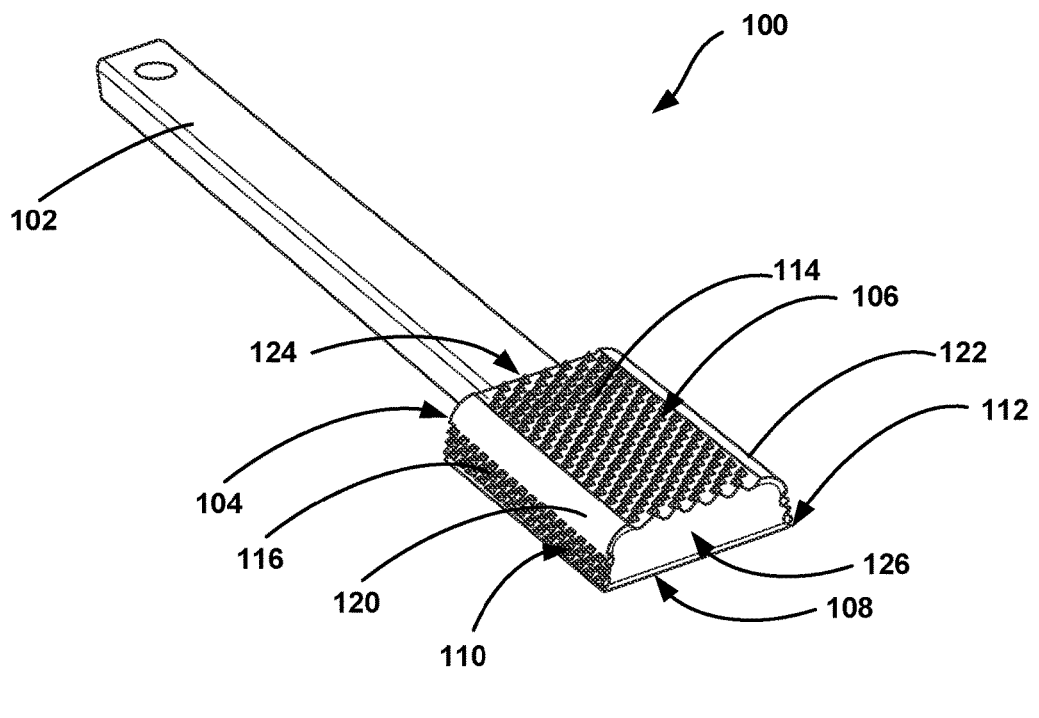
FIG. 1 is a perspective view of an example device.

With reference to the Figures, FIG. 1 illustrates a device 100 including a handle 102 and a rasp 104 coupled to the handle 102. The rasp 104 includes a top surface 106, a bottom surface 108, a first side surface 110, and a second side surface 112. A portion of the top surface 106 includes a first rough surface 114, a portion of the first side surface 110 includes a second rough surface 116, and a portion of the second side surface 112 includes a third rough surface 118. A first smooth curved surface 120 separates the first rough surface 114 from the second rough surface 116, and a second smooth curved surface 122 separates the first rough surface 114 from the third rough surface 118.

In an example, the bottom surface 108 is smooth. In another example, the bottom surface 108 is rough. In an example, the first rough surface 114 comprises a first plurality of spikes, the second rough surface 116 comprises a second plurality of spikes, and the third rough surface 118 comprises a third plurality of spikes. As shown in FIG. 1, the rasp 104 includes a first end 124 and a second end 126 opposite the first end 124. In one example, the first rough surface 114 extends from the first end 124 to the second end 126, the second rough surface 116 extends from the first end 124 to the second end 126, and the third rough surface 118 extends from the first end 124 to the second end 126. In such an example, the first smooth curved surface 120 extends from the first end 124 to the second end 126 and the second smooth curved surface 122 extends from the first end 124 to the second end 126.

Figure 2:
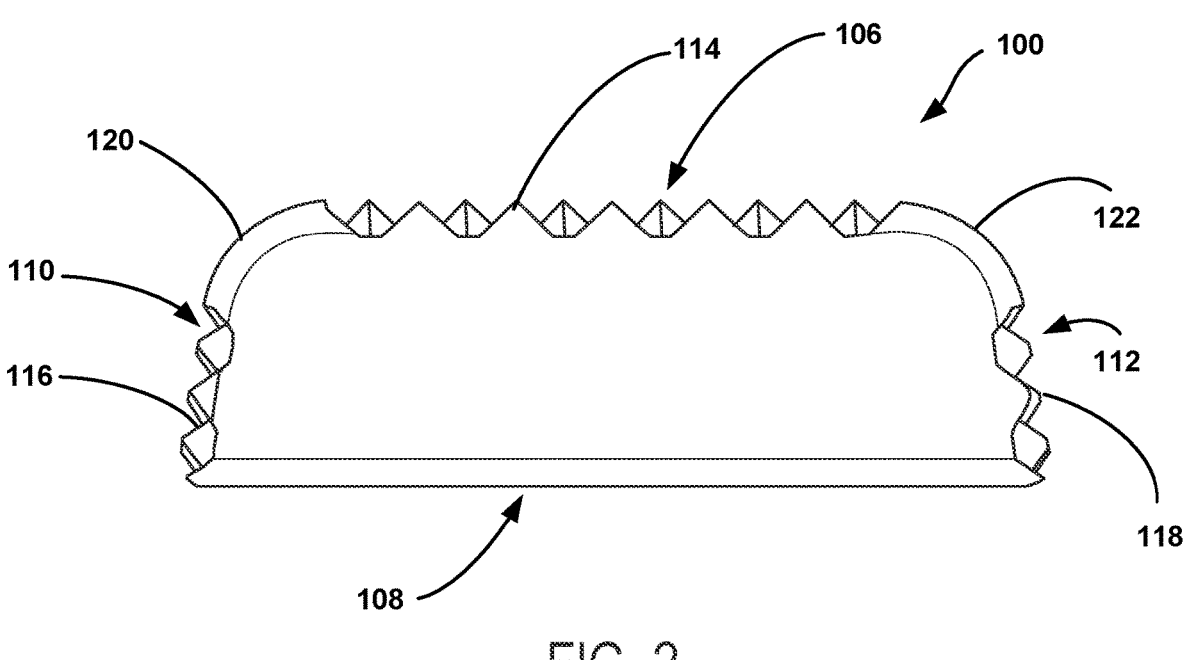
FIG. 2 is a front view of the example device of FIG. 1.

In an example, as shown in FIG. 2, an angle of the first side surface 110 relative to the top surface 106 is greater than 90 degrees, and an angle of the second side surface 112 relative to the top surface 106 is greater than 90 degrees. In an example, an angle of the first side surface 110 relative to the top surface 106 is equal to the angle of the second side surface 112 relative to the top surface 106. A diameter of the first smooth curved surface may be from about 0.5 to about 6.0 mm, and a diameter of the second smooth curved surface may be from about 0.5 to about 6.0 mm. A diameter of the first smooth curved surface can be about 0.5 mm, about 1.0 mm, about 1.5 mm, about 2.0 mm, about 2.25 mm, about 2.3 mm, about 2.5 mm, about 3.0 mm, about 3.5 mm, or about 4.0 mm. A diameter of the second smooth curved surface can be about 0.5 mm, about 1.0 mm, about 1.5 mm, about 2.0 mm, about 2.25 mm, about 2.3 mm, about 2.5 mm, about 3.0 mm, about 3.5 mm, or about 4.0 mm. The diameters of the first and second smooth curved surfaces can be the same or different.

As shown in FIG. 1, in an example, a width of the handle 102 is less than a width of the rasp 104. In another example, a bottom surface of the handle 102 aligns with the bottom surface 108 of the rasp 104.

In an example, the device 100 comprises a first device, and the device 100 has a first rough surface 114 including a first plurality of spikes, a second rough surface 116 including a second plurality of spikes, and a third rough surface 118 including a third plurality of spikes. A second device may be similarly configured to the device 100 described above, but the second device includes a fourth rough surface including a fourth plurality of spikes that is greater than the first plurality of spikes, a fifth rough surface including a fifth plurality of spikes that is greater than the second plurality of spikes, and a sixth rough surface including a sixth plurality of spikes that is greater than the third plurality of spikes. As such, the device 100 is configured with a lower grit to remove a bulk of excess material from the tibia, while the second device is configured with a higher grit to smooth out the tibia prior to implantation of the implant.

In an example, the rasp 104 is detachable from the handle 102. In such an example, the rasp 104 may comprise a first rasp having a first rough surface 114 including a first plurality of spikes, a second rough surface 116 including a second plurality of spikes, and a third rough surface 118 including a third plurality of spikes. A rasp may be configured to be removably attached to the handle 102, and the second rasp may be similarly configured to the rasp 104 described above, but the second rasp includes a fourth rough surface including a fourth plurality of spikes that is greater than the first plurality of spikes, a fifth rough surface including a fifth plurality of spikes that is greater than the second plurality of spikes, and a sixth rough surface including a sixth plurality of spikes that is greater than the third plurality of spikes. As such, the first rasp 104 is configured with a lower grit to remove a bulk of excess material from the tibia, while the second rasp is configured with a higher grit to smooth out the tibia prior to implantation of the implant.

Figures 3, 4, 5:
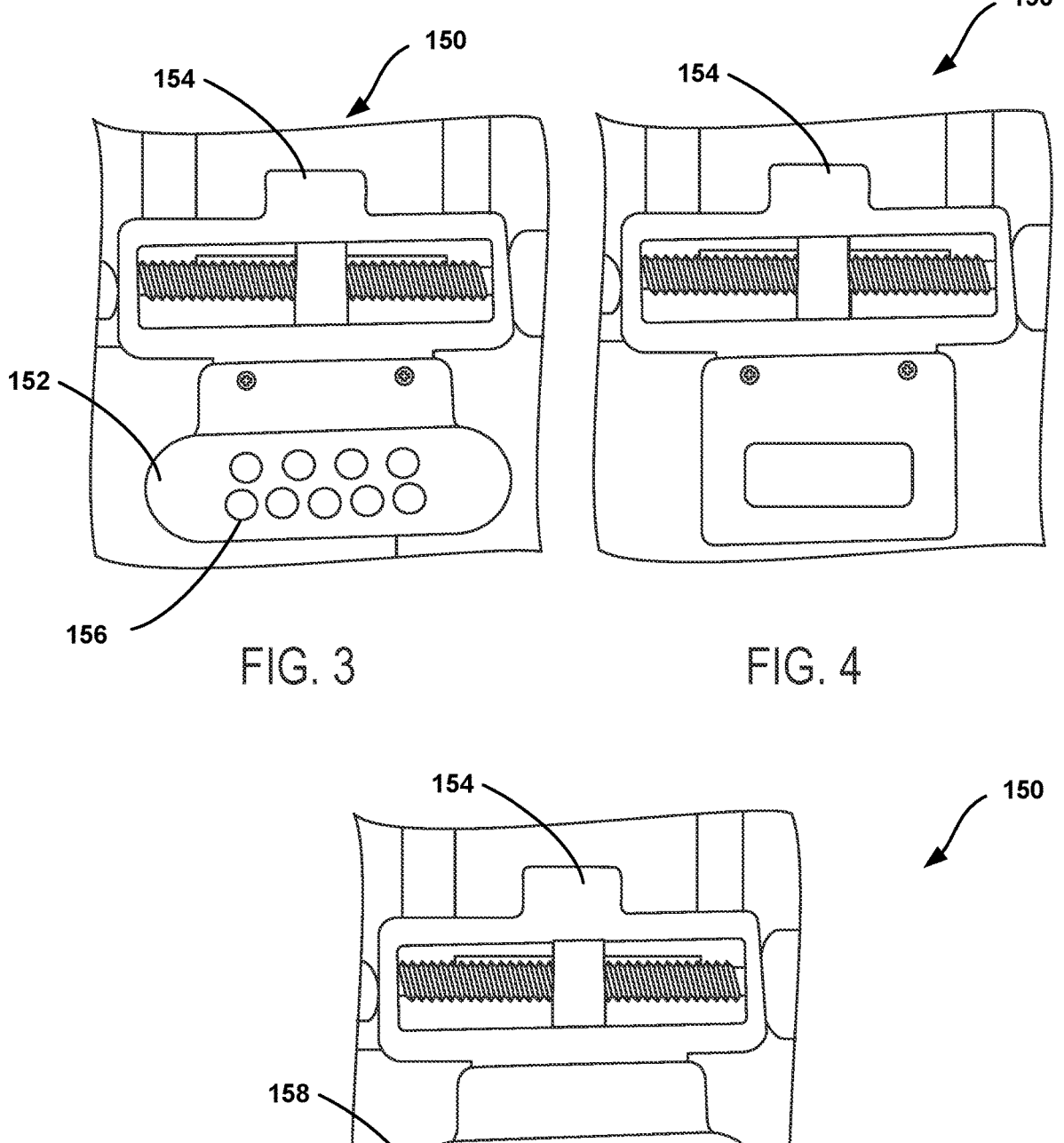
FIG. 3 is a front view of an example system including a first bushing coupled to a tibial external adjustment guide.
FIG. 4 is a front view of the example system of FIG. 3 with the first bushing removed from the tibial external adjustment guide after milling.
FIG. 5 is a front view of the example system of FIG. 3 including a second bushing.
Figure 6:
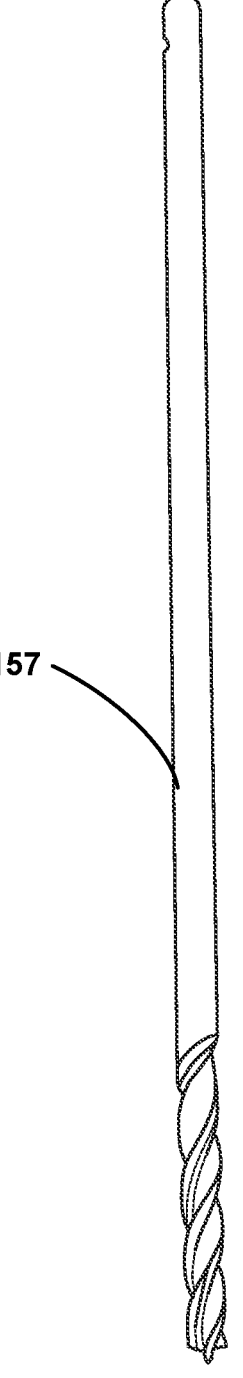
FIG. 6 is a side view of an example reamer.

FIGS. 3-5 show a system 150. The system 150 includes a first bushing 152 configured to be removably coupled to a tibia of a patient. As shown in FIG. 3, the first bushing 152 includes a first plurality of through-holes 156. As shown in FIG. 5, the system 150 also includes a second bushing 158 configured to be removably coupled to the tibia of the patient. The second bushing 158 includes a second plurality of through-holes 160. As shown in FIGS. 3-5, the first plurality of through-holes 156 and the second plurality of through-holes 160 may be cylindrical in shape to thereby receive a corresponding cylindrically shaped reamer 157 as discussed in additional detail below, and as shown in FIG. 6.

In an example, the first bushing 152 and the second bushing 158 are configured to be directly coupled to the tibia of the patient through fixation pins that are inserted into the tibia. In an example, the location of the fixation pins are established during preoperative planning and then transferred to the tibia during surgery.

In another example, a tibial external adjustment guide 154 is directly attached to the tibia of the patient, and the first bushing 152 and the second bushing 158 are configured to be coupled to the tibial external adjustment guide 154 such that the first bushing 152 and the second bushing 158 are indirectly coupled to the tibia.

In an example, a diameter of one or more of the first plurality of through-holes 156 are different from one another, and a diameter of one or more of the second plurality of through-holes 160 are the different from one another. In another example, a diameter of each of the first plurality of through-holes 156 are the same, and wherein a diameter of each of the second plurality of through-holes 160 are the same. A diameter of each of the first plurality of through-holes 156 can be greater than the diameter of each of the second plurality of through-holes 160. Also, the diameter of each of the first plurality of through-holes 156 can be less than the diameter of each of the second plurality of through-holes 160. As shown in FIGS. 3 and 5, the first plurality of through-holes 156 may be offset from the second plurality of through-holes 160. As such, the first plurality of through-holes 156 line up with a first plurality of areas of the tibia of a patient, and the second plurality of through-holes 160 line up with a second plurality of areas of the tibia of a patient.

Figures 7, 8, 9:
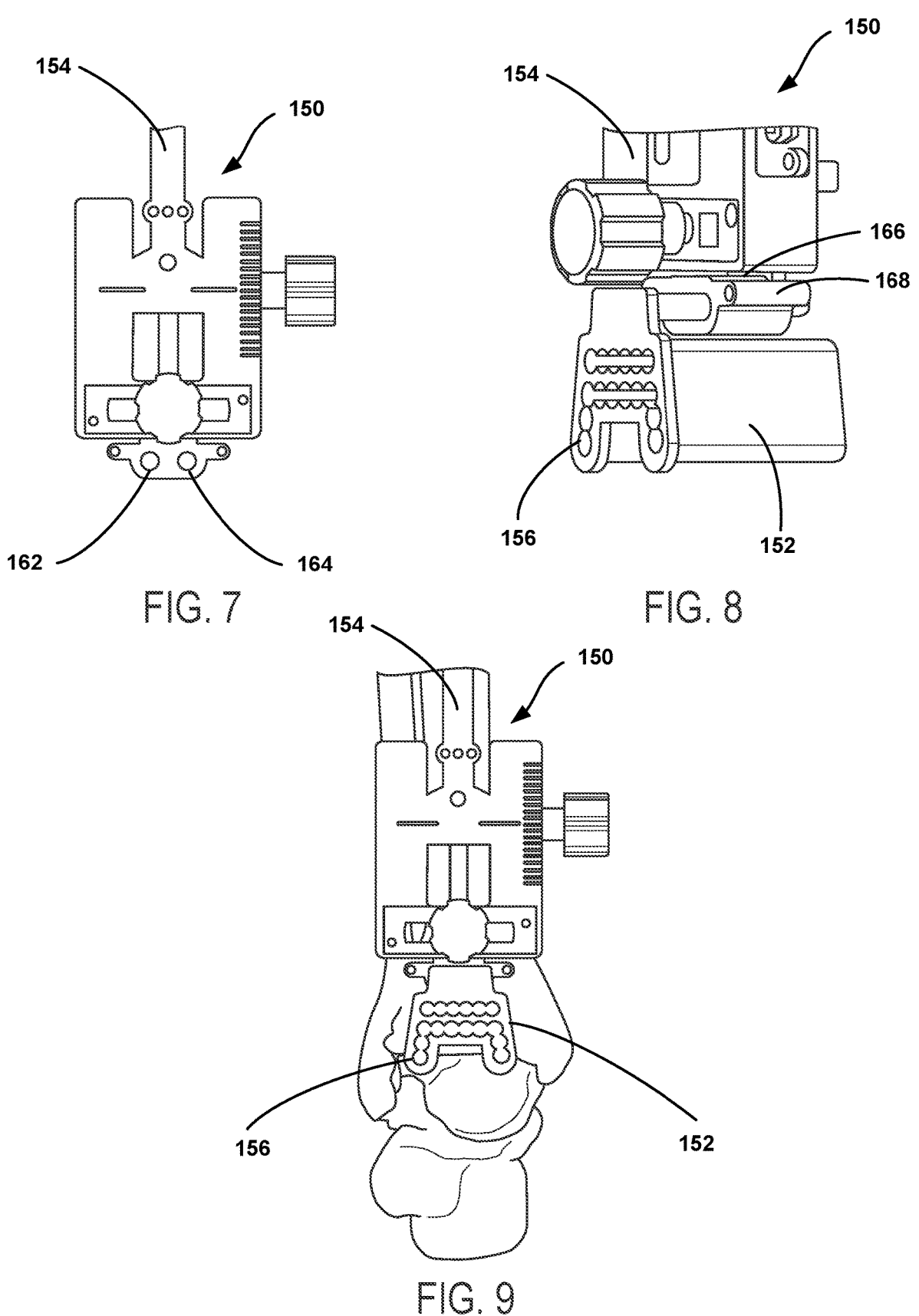
FIG. 7 is a front view of an example tibial external adjustment guide.
FIG. 8 is a perspective view of a first bushing positioned in the example tibial external adjustment guide of FIG. 6.
FIG. 9 is a front view of a first bushing positioned in the example tibial external adjustment guide of FIG. 6.

FIGS. 7-9 illustrate another example system 150. As shown in FIG. 6, in an example, a tibial external adjustment guide 154 includes a first through-hole 162 and a second through-hole 164. In such an example, as shown in FIG. 8, the first bushing 152 may include a first elongated member 166 configured to be removably positioned through the first through-hole 162 of the tibial external adjustment guide 154, and the first bushing 152 includes a second elongated member 168 configured to be removably positioned through the second through-hole 164 of the tibial external adjustment guide 154. In such an example, the second bushing 158 may be similarly configured with a first elongated member 166 and a second elongated member 168 configured to be removably positioned through the first through-hole 162 and second through-hole 164, respectively. In another example, a first elongated member 166 and a second elongated member 168 of the first bushing 152 each include a canted coil spring to thereby removably couple the first bushing 152 to the tibial external adjustment guide 154. In such an example, the elongated members of the second bushing 158 may each be similarly configured with a canted coil spring to thereby removably couple the second bushing 158 to the tibial external adjustment guide 154. In another example, the first through-hole 162 of the tibial external adjustment guide 154 and the second through-hole 164 of the tibial external adjustment guide 154 each include a canted coil spring to thereby removably couple the first bushing 152 and the second bushing 158 to the tibial external adjustment guide 154.

In an example, as shown in FIGS. 10-11, in the first bushing 152, a first through-hole of the first plurality of through-holes 156 may be tangent to and/or slightly overlapping a second through-hole of the first plurality of through-holes 156. Similarly, in the second bushing 158, a first through-hole of the second plurality of through-holes 160 may be tangent to and/or slightly overlapping a second through-hole of the second plurality of through-holes 160. Such an arrangement helps to maximize the amount of tibial material that is removed during plunge milling.

In an example, as shown in FIG. 10-11, the first plurality of through-holes 156 are positioned proximal relative to the second plurality of through-holes 160. As such, the first plurality of through-holes 156 define a top surface of the resection of the tibia into which an implant is positioned.

In one example, a guide is used when using the device 100. Such a guide may be attached to the tibial external adjustment guide 154 in a similar fashion as the first bushing 152 and the second bushing 158 are attached. In another example, the guide for the device 100 may be attached directly over two pins that are placed in the distal tibia.

As shown in FIG. 13, the system 150 can further include a patient specific disposable surface 170 that is configured to be removably coupled to a first side of the first bushing 152. The patient specific disposable surface 170 provides good a contact surface with the anterior surface of the distal tibia of the patient, thus stabilizing the first bushing 152 during the reaming process. As shown in FIG. 12, the patient specific disposable surface 170 may be created by taking geometry or data points via preoperative computed tomography and/or via magnetic resonance imaging data. Such data can then be transposed to the mating surface 172 of the patient specific disposable surface 170. The patient specific disposable surface 170 is configured to be positioned on a non-articulating surface of the ankle. In one example, the patient specific disposable surface 170 is positioned on a unique feature of the tibia, and then pinned in place, thereby removing the need for any additional alignment steps.

In FIG. 14, the patient specific disposable surface 170 is shown removably attached to the first side of the first bushing 152. Further, as shown in FIG. 14, when in use a reamer 157 is configured to be plunged through the first plurality of through-holes 156, through the patient specific disposable surface 170, and into the tibia of the patient. After reaming, the patient specific disposable surface 170 can be removed from the reusable first bushing 152, and the patient specific disposable surface 170 can be discarded.

Figures 15, 16:
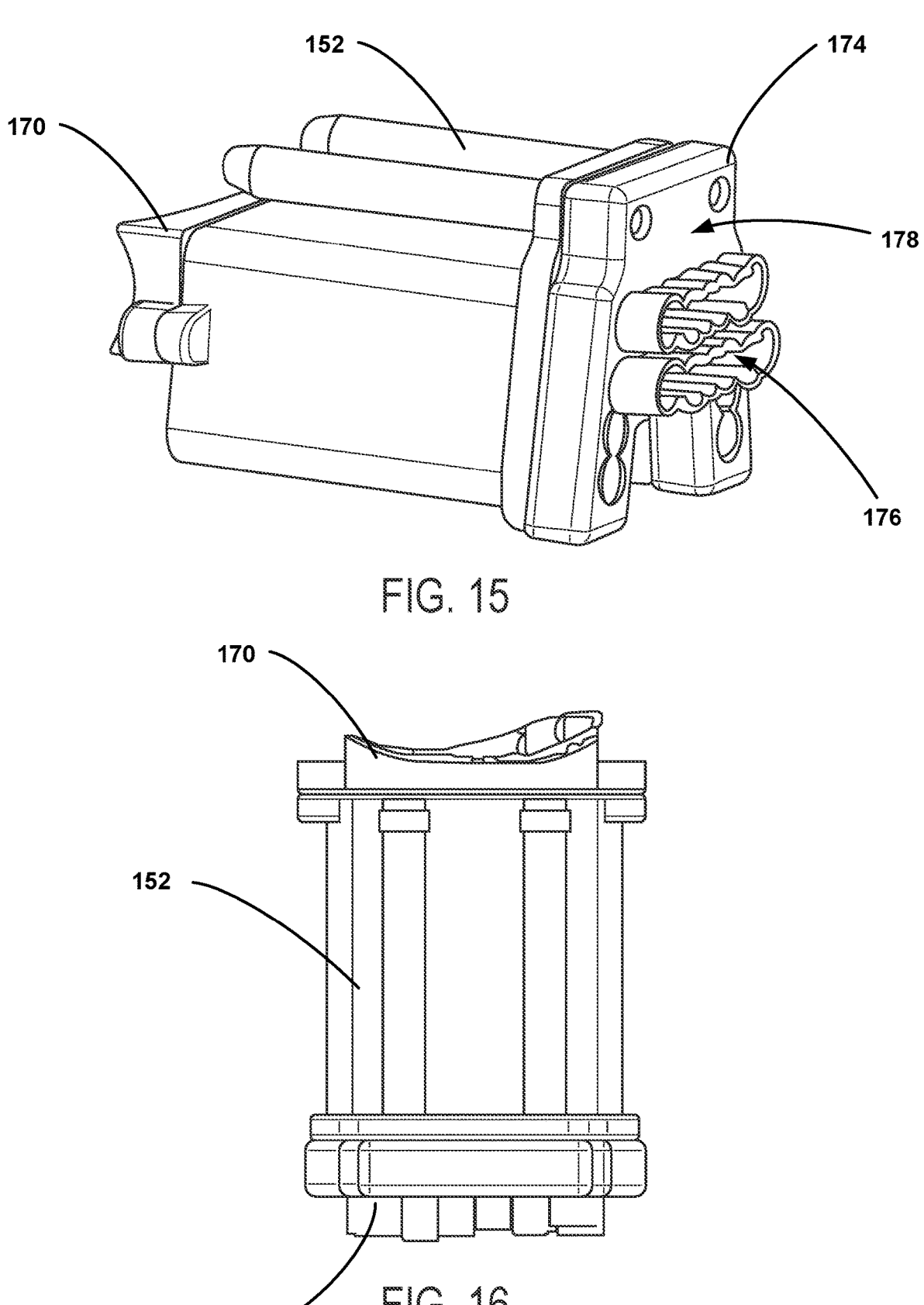
FIG. 15 is a perspective view of a bushing with patient specific disposable surface removably coupled to a first side of the busing and a patient specific depth guide removably coupled to a second side of the bushing.
FIG. 16 is a top view of the bushing of FIG. 15.

As shown in FIGS. 15-16, the system 150 can further include a patient specific depth guide 174 that is configured to be removably coupled to a second side of the first bushing 152. The patient specific depth guide 174 includes a plurality of through-holes 176 that align with the first plurality of through-holes 156 of the first bushing 152. As shown in FIGS. 15-16, the plurality of through-holes 176 of the patient specific depth guide 174 extend away from the surface 178 of the patient specific depth guide 174 at varying distances. As such, the patient specific depth guide 174 provides varying depths for reamer 157 plunging based on the anterior-posterior depth of the patient's anatomy. The varying depth of the patient specific depth guide 174 is for the purpose of the reamer 157 to have a positive stop before plunging too far posterior. These varying depths are determined during the preoperative planning and with both patient matched guides attached to the first bushing 152 the reamer 157 would have a fixed positive stop based on the varying patient's anatomy. The varying depths of the patient specific depth guide 174 correspond to a distance measured anterior to posterior length of the tibia to prevent the reamer 157 from being over plunged. In such an example, the anterior to posterior length of the tibia may be measured directly through the first hole via a depth gauge, via preoperative computed tomography, and/or via magnetic resonance imaging data.

The patient specific disposable surface 170 and the patient specific depth guide 174 may be created for each individual patient, and are each configured to be removably coupled to the first bushing 152. After use, the patient specific disposable surface 170 and the patient specific depth guide 174 can be discarded, while the first bushing 152 can be reused for multiple procedures and multiple patients.

In an example, the system 150 further includes a second patient specific disposable surface that is configured to be removably coupled to a first side of the second bushing 158. The system also includes a second patient specific depth guide that is configured to be removably coupled to a second side of the second bushing 158. The second patient specific depth guide includes a plurality of through-holes that align with the second plurality of through-holes 160 of the second bushing 158. In another example, the patient specific disposable surface 170 may be reused with the second bushing 158, while a new second patient specific depth guide is used with the second bushing 158.

A kit for resecting a tibial bone is also disclosed. A kit includes a device 100 and a system 150 as described herein. In addition, a kit may include a reamer 157. The reamer 157 can be configured to be positioned through the first plurality of through-holes 156 of the first bushing 152. In one example, the reamer 157 can be further configured to be positioned through the second plurality of through-holes 160 of the second bushing 158. In an example, the diameter of the reamer 157 is equal to a diameter of a first smooth curved surface and a diameter of the second smooth curved surface. In an example, a diameter of the reamer 157 is 4.5 mm. In another example, a kit can further include a depth stop configured to be removably coupled to the reamer 157 to provide a positive stop to thereby define a reamer depth. In one example, a depth stop comprises a lockable collar. In another example, a kit can further include a second reamer having a second diameter that is different than the diameter of the reamer 157. In such an example, the second reamer can be configured to be positioned through the second plurality of through-holes 160 of the second bushing 158.

Figure 17:
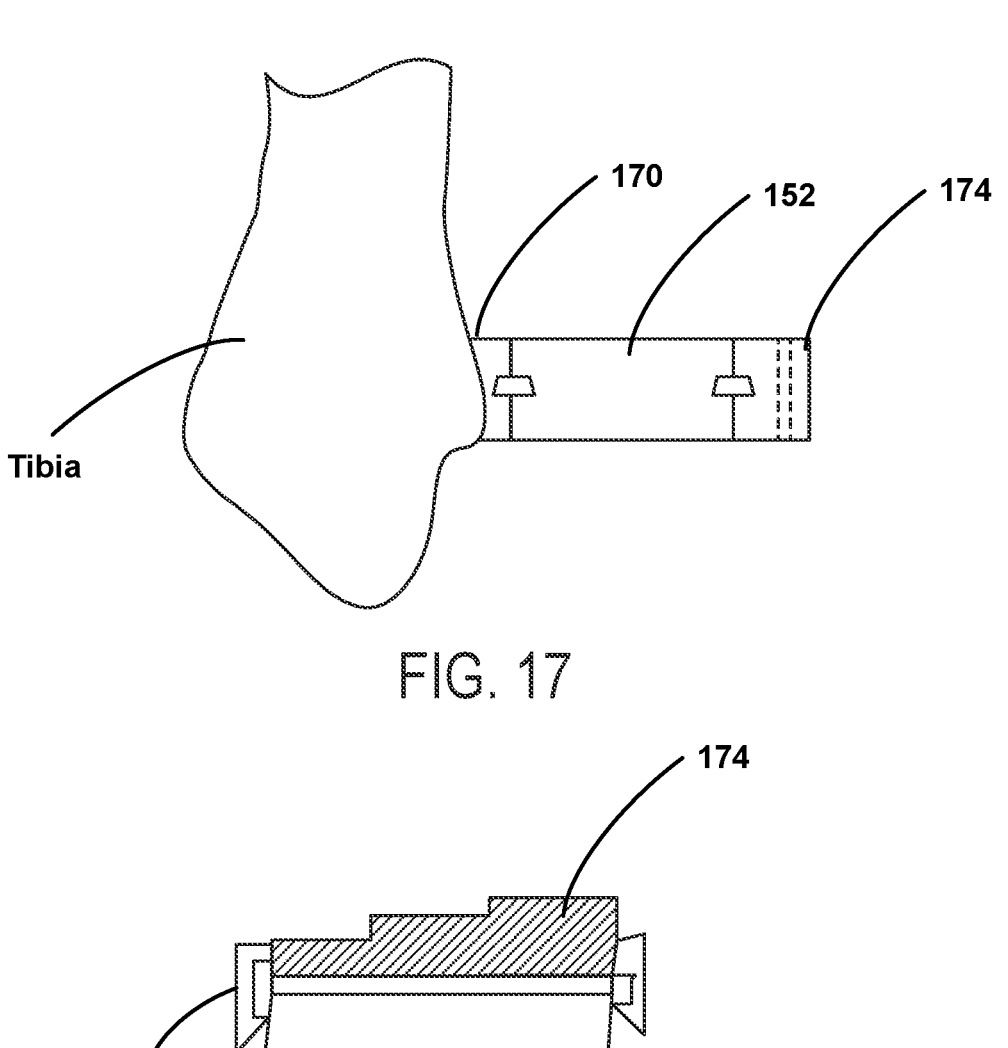
FIG. 17 is a lateral view of the system of FIG. 15 positioned on a tibia of a patient.
Figure 18:
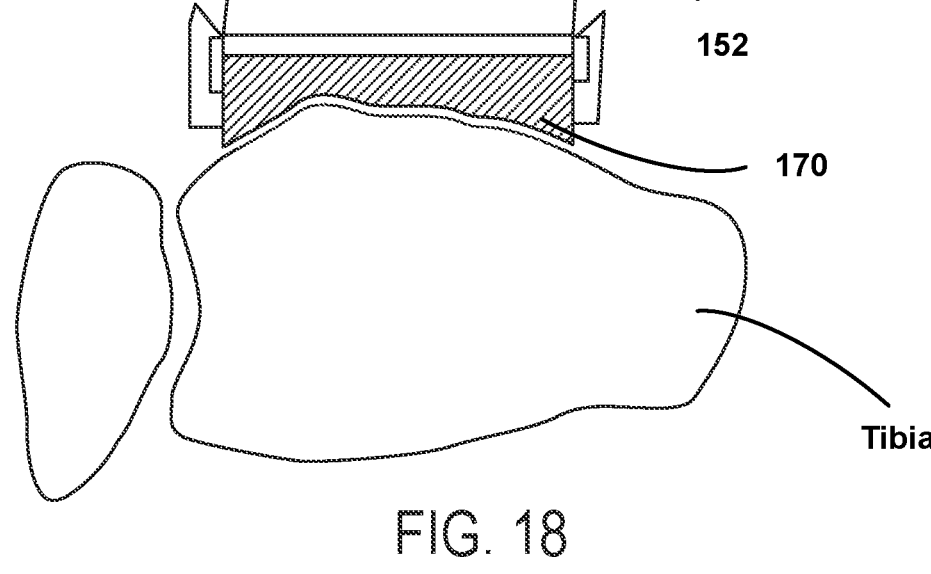
FIG. 18 is an axial view of the system of FIG. 15 positioned on a tibia of a patient.

FIG. 17 illustrates a lateral view of the system of FIG. 15 positioned on a tibia of a patient, while FIG. 18 illustrates an axial view of the system of FIG. 15 positioned on the tibia of a patient. As shown in FIGS. 17-18, in an example the patient specific disposable surface 170 and the patient specific depth guide 174 and coupled to the first bushing 152 and the second bushing 158 via clips 180. Other removable coupling mechanisms between these component are possible as well.

Figure 19:
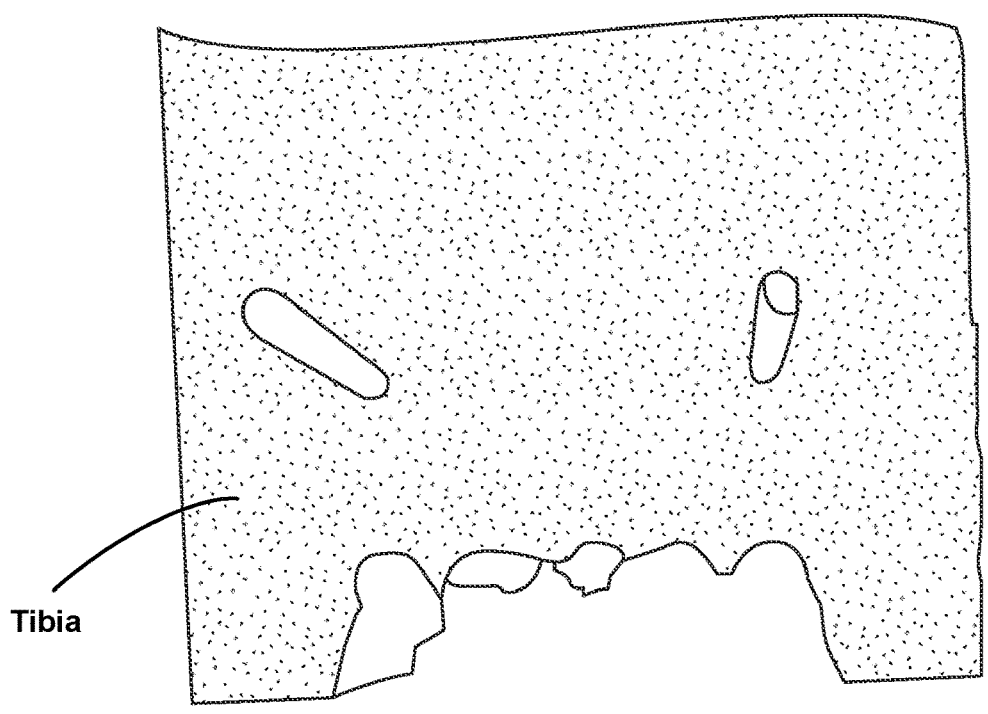
FIG. 19 is a front view of a tibia after milling.
Figure 20:
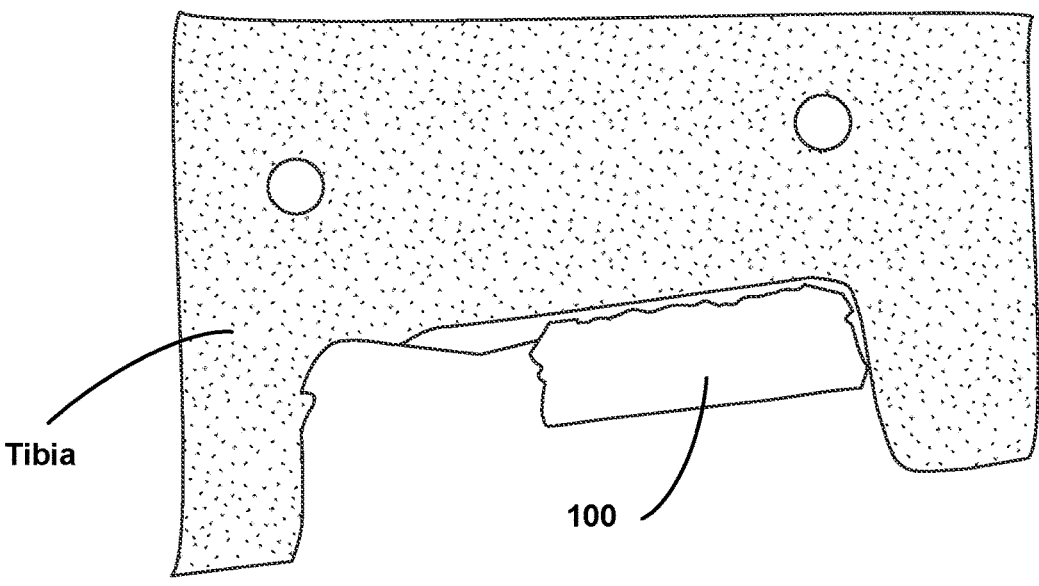
FIG. 20 is a front view of the tibia of FIG. 19 after rasping using the device of FIG. 1.

FIG. 19 illustrates a tibia of a patient after a reamer 157 is plunged through a first plurality of through-holes 156 and the reamer 157 is plunged through a second plurality of through-holes 160. FIG. 20 illustrates the device 100 of FIGS. 1-2 rasping a tibia to file down the remaining ridges left behind by the reaming process.

Methods disclosed herein can be used with any of the embodiments of the device 100, the system 150, and the kit as described herein.

A method of preparing a tibia for an implant includes removably coupling a first bushing 152 to a tibia of a patient, where the first bushing 152 includes a first plurality of through-holes 156. A method can also include plunging a reamer 157 through the first plurality of through-holes 156 and into the tibia. The first bushing 152 can then be removed from the tibia of the patient. A method can also include removably coupling a second bushing 158 to the tibia of the patient, where the second bushing includes a second plurality of through-holes 160. A method can also include plunging the reamer 157 through the second plurality of through-holes 160 and into the tibia. The second bushing 158 can then be removed from the tibia of the patient. A method can also include removing additional tibia material using the device 100 as described herein.

As described above, the device 100 is designed to smooth out any remaining bone material left behind by the milling process. Medial and lateral corners of the device 100 are polished smooth, making them incapable of gouging or digging into bone during rasping. These smooth medial and lateral corners match the placement of the two corner drill holes of the bushing and act as a guide for the device 100. These features mitigate the risk of over-rasping and removing more bone than is desired.

In an example, a diameter of the reamer 157 is equal to a diameter of the first smooth curved surface 120 and a diameter of the second smooth curved surface 122. The first smooth curved surface 120 and the second smooth curved surface 122 act as a depth stop to help prevent the user from rasping excessively and in turn removing too much bone.

In an example, a method further includes measuring an anterior to posterior length of the tibia, and providing a depth stop to the reamer 157 at a distance corresponding to the measured anterior to posterior length of the tibia to prevent the reamer 157 from being over plunged. In such an example, the anterior to posterior length of the tibia may be measured directly through the first hole via a depth gauge, via preoperative computed tomography, and/or via magnetic resonance imaging data.

In an example, a method further includes securing one or more fixation pins to the tibia of the patient. In such an example, the first bushing 152 and the second bushing 158 are configured to be directly coupled to the tibia of the patient through fixation pins that are inserted into the tibia. In an example, the location of the fixation pins are established during preoperative planning and then transferred to the tibia during surgery.

In an example, a method further includes securing a tibial external adjustment guide 154 to the tibia of the patient. In such an example, the first bushing 152 and the second bushing 158 are configured to be coupled to the tibial external adjustment guide 154 such that the first bushing 152 and the second bushing 158 are indirectly coupled to the tibia.

In another example, a method of preparing a tibia for an implant includes removably coupling a first bushing 152 to a tibia of a patient. The first bushing 152 includes a first plurality of through-holes 156. A method can also include removably coupling a patient specific disposable surface 170 to a first side of the first bushing 152. A method can also include removably coupling a patient specific depth guide 174 to a second side of the first bushing 152. The patient specific depth guide 174 includes a plurality of through-holes 176 that align with the first plurality of through-holes 156 of the first bushing 152. A method can also include plunging a reamer 157 through the first plurality of through-holes 156, through the patient specific disposable surface 170, and into the tibia of the patient.

A method can also include removing the first bushing 152 from the tibia of the patient. A method can also include coupling a second bushing 158 to the tibia of the patient. The second bushing 158 includes a second plurality of through-holes 160. A method can also include removably coupling a second patient specific disposable surface to a first side of the second bushing 158. A method can also include removably coupling a second patient specific depth guide to a second side of the second bushing 158. The second patient specific depth guide includes a plurality of through-holes that align with the second plurality of through-holes 160 of the second bushing 158. A method can also include plunging a reamer 157 through the second plurality of through-holes 160, through the second patient specific disposable surface, and into the tibia of the patient. The second bushing 158 can then be removed from the tibia of the patient.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and examples have been disclosed herein, other aspects and examples will be apparent to those skilled in the art. The various aspects and examples disclosed herein are for purposes of illustration and are not intended to be limiting, with the true scope being indicated by the following claims, along with the full scope of equivalents to which such claims are entitled. It is also to be understood that the terminology used herein is for the purpose of describing particular examples only, and is not intended to be limiting.

Example methods and systems are described herein. It should be understood that the words "example," "exemplary," and "illustrative" are used herein to mean "serving as an example, instance, or illustration." Any example or feature described herein as being an "example," being "exemplary," or being "illustrative" is not necessarily to be construed as preferred or advantageous over other examples or features. The examples described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other examples may include more or less of each element shown in a given Figure. Further, some of the illustrated elements may be combined or omitted. Yet further, an example may include elements that are not illustrated in the Figures.

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

As used herein, "coupled" means associated directly as well as indirectly. For example, a member A may be directly associated with a member B, or may be indirectly associated therewith, e.g., via another member C. It will be understood that not all relationships among the various disclosed elements are necessarily represented.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" means that one or more feature, structure, or characteristic described in connection with the example is included in at least one implementation. The phrases "one embodiment" or "one example" in various places in the specification may or may not be referring to the same example.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification.

For purposes of this disclosure, a system, apparatus, structure, article, element, component, or hardware described as being "configured to" perform a particular function may additionally or alternatively be described as being "adapted to" and/or as being "operative to" perform that function.

The limitations of the following claims are not written in means-plus-function format and are not intended to be interpreted based on 35 U.S.C. § 112(f), unless and until such claim limitations expressly use the phrase "means for" followed by a statement of function void of further structure.

By the term "about," "approximately," or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. For example, in one embodiment, the term "about" can refer to ±5% of a given value.

Illustrative, non-exhaustive examples, which may or may not be claimed, of the subject matter according the present disclosure are provided below.

What is claimed is:

1. A device comprising:

a handle; and a rasp coupled to the handle, wherein the rasp includes a top surface, a bottom surface, a first side surface, and a second side surface, wherein a portion of the top surface includes a first rough surface, wherein a portion of the first side surface includes a second rough surface, wherein a portion of the second side surface includes a third rough surface, wherein a first smooth curved surface separates the first rough surface from the second rough surface, wherein a second smooth curved surface separates the first rough surface from the third rough surface, wherein the first and second curved surfaces are configured to limit a rasping depth, wherein the first rough surface comprises a first plurality of spikes each including a corresponding peak, wherein a distance between a top portion of the first smooth surface and the bottom surface is at least as great as a maximum distance between the peaks of the first plurality of spikes and the bottom surface, and wherein a diameter of the first smooth curved surface ranges from about 0.5 to about 6.0 mm, and wherein a diameter of the second smooth curved surface ranges from about 0.5 to about 6.0 mm.

2. The device of claim 1, wherein the bottom surface is smooth.

3. The device of claim 1, wherein the bottom surface is rough.

4. The device of claim 1, wherein the second rough surface comprises a second plurality of spikes, and wherein the third rough surface comprises a third plurality of spikes.

5. The device of claim 1, wherein the rasp includes a first end and a second end opposite the first end, wherein the first rough surface extends from the first end to the second end, wherein the second rough surface extends from the first end to the second end, and wherein the third rough surface extends from the first end to the second end.

6. The device of claim 1, wherein an angle of the first side surface relative to the top surface is greater than 90 degrees, and wherein an angle of the second side surface relative to the top surface is greater than 90 degrees.

7. The device of claim 1, wherein a width of the handle is less than a width of the rasp.

8. The device of claim 1, wherein a bottom surface of the handle aligns with the bottom surface of the rasp.

9. The device of claim 1, wherein both of the first curved surface and the second curved surface are polished smooth.

10. The device of claim 1, wherein the rasp is configured to extend into a negative space defined in a bone.

11. The device of claim 10, wherein the negative space is at least partially defined by a smooth corner, wherein a radius of curvature of the first curved surface is equal to a radius of curvature of the smooth corner.

12. The device of claim 10, wherein a contact between the first curved surface and a corresponding surface of the bone prevents a contact between the first rough surface and the bone.

13. The device of claim 1, wherein the diameter of the first curved surface is about 4.5 mm.

\* \* \* \* \*